(12) United States Patent
Boisvert

(10) Patent No.: US 9,522,200 B2
(45) Date of Patent: Dec. 20, 2016

(54) SANITATION APPARATUS FOR BUTTONS

(71) Applicant: GESTION RAYMOND BOISVERT INC., Quebec (CA)

(72) Inventor: Raymond Boisvert, Quebec (CA)

(73) Assignee: GESTION RAYMOND BOISVERT INC., Quebec (CA)

(\*) Notice: Subject to any disclaimer, the term of this patent is extended or adjusted under 35 U.S.C. 154(b) by 0 days.

(21) Appl. No.: 14/408,141

(22) PCT Filed: Jun. 13, 2013

(86) PCT No.: PCT/CA2013/050450
§ 371 (c)(1),
(2) Date: Dec. 15, 2014

(87) PCT Pub. No.: WO2013/185233
PCT Pub. Date: Dec. 19, 2013

(65) Prior Publication Data
US 2015/0151016 A1    Jun. 4, 2015

Related U.S. Application Data

(60) Provisional application No. 61/658,919, filed on Jun. 13, 2012.

(51) Int. Cl.
*A61L 2/10* (2006.01)
*A47L 25/02* (2006.01)
(Continued)

(52) U.S. Cl.
CPC .............. *A61L 2/10* (2013.01); *A47L 25/02* (2013.01); *B08B 7/0057* (2013.01); *B66B 1/466* (2013.01)

(58) Field of Classification Search
None
See application file for complete search history.

(56) References Cited

U.S. PATENT DOCUMENTS 3,314,746 A    4/1967 Millar
4,046,508 A    9/1977 McDonald
(Continued)

FOREIGN PATENT DOCUMENTS

CN    102050364 A  *  5/2011  ............... A61L 2/18
JP    2006240789 A  *  9/2006  ............... B66B 1/50
(Continued)

OTHER PUBLICATIONS

AusCan531,"Simple Elevator Button Sterilizer Design", http://www.halfbakery.com/idea/Simple_20Elevator_20Button_20Sterilizer_20Design/addlink#addlink, Dec. 13, 2011.*
(Continued)

*Primary Examiner* — Michael Logie
(74) *Attorney, Agent, or Firm* — St. Onge Steward Johnston and Reens

(57) ABSTRACT

An apparatus for disinfecting a button including a housing having an inner side and an outer side. At least one button is disposed within the housing, the button having a rotational symmetry allowing rotation of the button with respect to the housing. A rotation mechanism rotates the button with respect to the housing. A disinfecting system positioned on the inner side of the housing disinfects a portion of the button that is exposed on the inner side of the housing. The rotation mechanism rotates the button at a substantially constant speed. The apparatus provides a safer operation of the button as there is a continuous sanitizing of the surface of the button contaminated by users.

18 Claims, 12 Drawing Sheets

(51) Int. Cl.
    *B08B 7/00*     (2006.01)
    *B66B 1/46*     (2006.01)

(56)  References Cited

U.S. PATENT DOCUMENTS

| | | | |
|---|---|---|---|
| 5,914,466 A * | 6/1999 | Durand | H03K 17/968 |
| | | | 187/391 |
| 7,598,501 B2 | 10/2009 | Jones | |
| 7,692,172 B2 | 4/2010 | Leben | |
| 2005/0011042 A1 | 1/2005 | Hupp et al. | |
| 2007/0071636 A1* | 3/2007 | Bovino | A61L 2/08 |
| | | | 422/24 |
| 2007/0145292 A1* | 6/2007 | Jones | A61L 2/10 |
| | | | 250/453.11 |
| 2009/0308399 A1* | 12/2009 | Niemi | A61F 6/04 |
| | | | 128/830 |
| 2012/0131756 A1 | 5/2012 | Gilsenan et al. | |
| 2013/0200279 A1* | 8/2013 | Chuang | B66B 1/466 |
| | | | 250/492.1 |

FOREIGN PATENT DOCUMENTS

| | | | | |
|---|---|---|---|---|
| JP | 2011143994 A * | 7/2011 | | B66B 1/46 |
| JP | CN 202061125 U * | 12/2011 | | A61L 2/18 |
| WO | 2008035121 A1 | 3/2008 | | |

OTHER PUBLICATIONS

International Search Report and Written Opinion of the International Searching Authority Application No. PCT/CA2013/050450 Completed: Aug. 8, 2013; Mailing Date: Aug. 30, 2013 6 pages.

\* cited by examiner

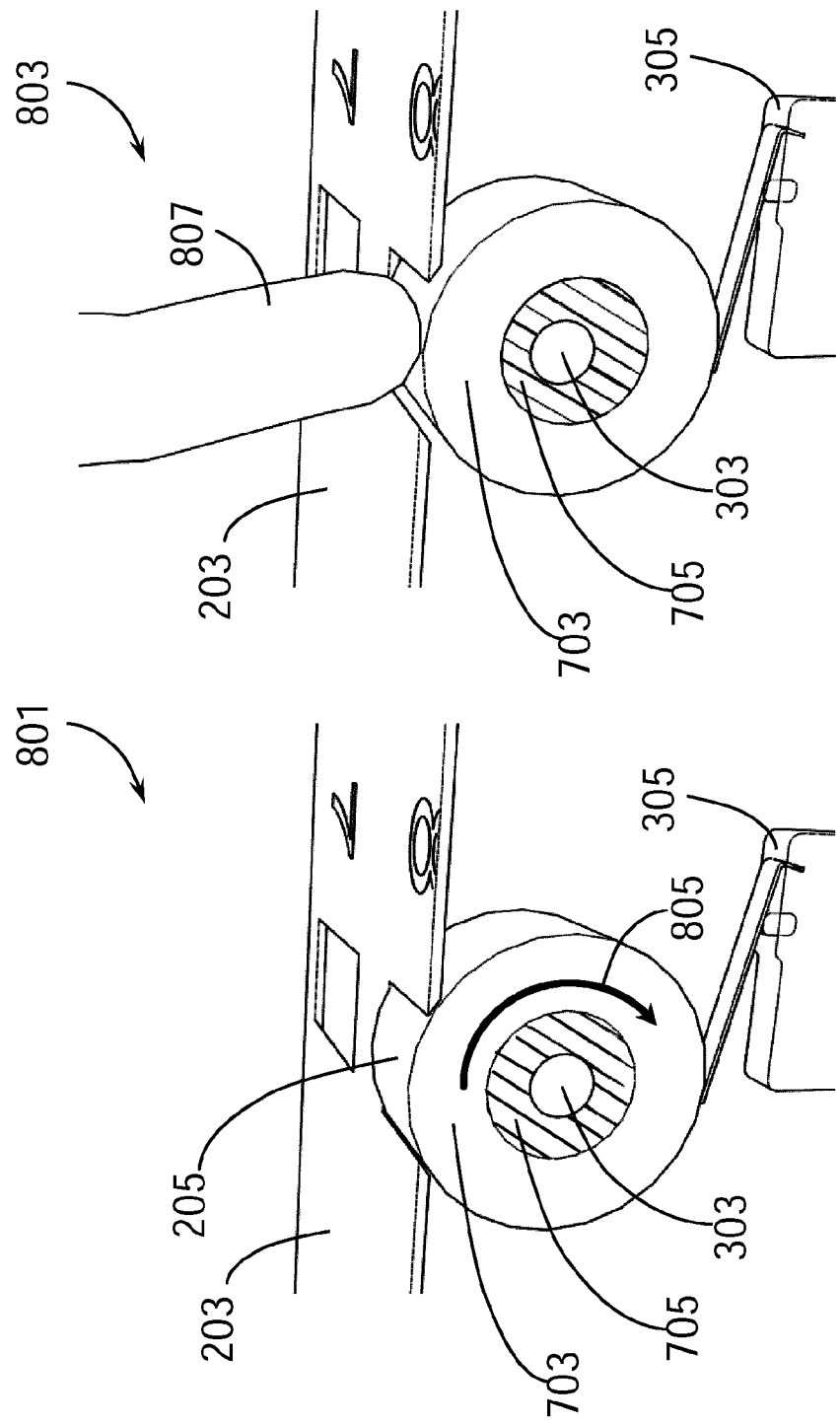

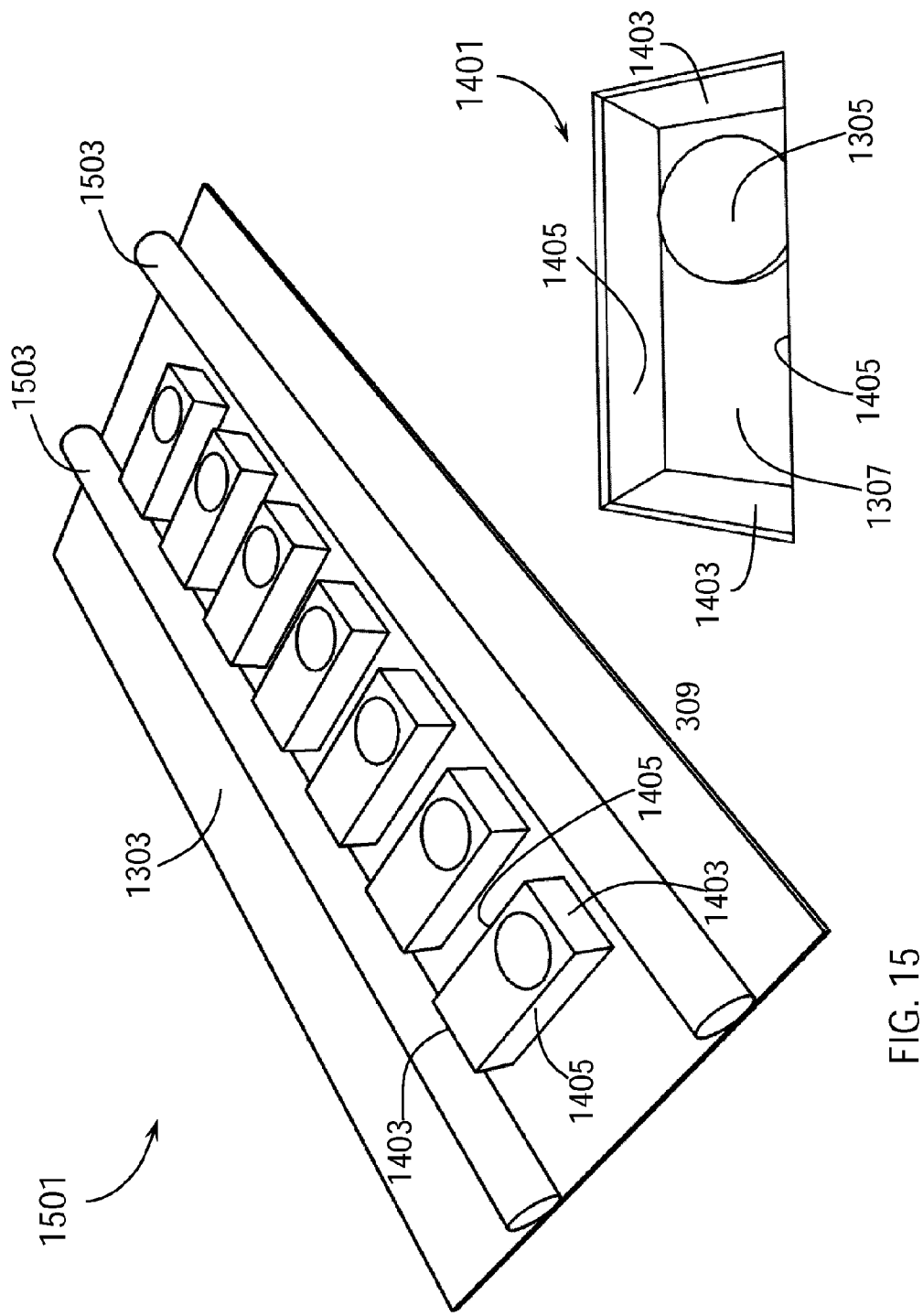

SANITATION APPARATUS FOR BUTTONS

TECHNICAL FIELD

This invention relates to the field of sanitation using UV (Ultraviolet) light with or without the addition of chemical disinfectants and more particularly to an apparatus for the sanitation of buttons, for example, elevator buttons.

BACKGROUND OF THE ART

Elevators are convenient apparatus for humans working or living in high-rise buildings. Modern elevators carry people and goods on any floor rapidly and securely.

Most elevator use sophisticated control systems that respond primarily to floor requests by way of buttons installed on user panels. The vast majority of these panels actually requires the user to physically touch and press the buttons, allowing germs and bacteria to be transferred from hands to the buttons and from the buttons to hands.

New findings show that the number of bacteria present on an elevator button is almost 40 times higher than on public toilet seats. Research carried out in public areas showed that the level of bacteria on elevator buttons can average up to 313 colony forming units (CFUs) per square centimeter, compared to 8 CFUs on the average public toilet seat. *E. coli, Staphylococcus aureus* and methicillin-resistant *Staphylococcus aureus* are some of the common bacteria that can be found on elevator buttons. It is known that direct hand contact is one important method by which germs and bacteria spread through the population and that contributes to increased risk of contamination and disease.

The prior art button panels systems have many drawbacks and limitations.

Some of the prior art systems known to the Applicant are disclosed in patent documents U.S. Pat. No. 7,598,501, U.S. Pat. No. 7,692,172, US20070071636 and US20120131756.

There is thus a need to provide an efficient apparatus for sanitizing buttons, such as elevator buttons.

SUMMARY OF THE INVENTION

An object of the invention is to provide an apparatus that addresses at least one of the above-mentioned needs.

According to the invention, there is provided an apparatus for disinfecting a button comprising:
 a housing having an inner side and an outer side;
 at least one button disposed within the housing, the button having a rotational symmetry allowing rotation of the button with respect to the housing;
 a rotation mechanism for rotating the button with respect to the housing; and
 a disinfecting system positioned on the inner side of the housing for disinfecting a portion of the button that is exposed on the inner side of the housing,
wherein the rotation mechanism rotates the button at a substantially constant speed.

The apparatus provides a safer operation of the button as there is a continuous, yet imperceptible, sanitizing of the surface of the button contaminated by users.

BRIEF DESCRIPTION OF THE DRAWINGS

Having thus generally described the nature of the invention, reference will now be made to the accompanying drawings, showing by way of illustration example embodiments thereof and in which

FIG. 8A is a cutout view of one button of the example user panel viewed in FIG. 2, FIG. 3, FIG. 4, FIG. 5, FIG. 6 and FIG. 7 showing the inner parts of the button;

FIG. 8B is a cutout view of the button viewed in FIG. 8A, when a user presses on the button;

FIG. 14 is a detailed perspective view of one button of the example user panel viewed in FIG. 13A and FIG. 13B, inside its recess;

FIG. 15 is a rear perspective view of the example user panel viewed in FIG. 13A, FIG. 13B and FIG. 14, showing two germicidal lamps;

It will be noted that throughout the appended drawings, like features are identified by like reference numerals.

DETAILED DESCRIPTION

The present invention discloses multiple systems and methods for sanitizing elevator buttons using germicidal UV (Ultraviolet) light with or without the use of additional disinfection method such chemical disinfectants. The same systems and methods could also be applied to other user panels where humans press buttons including but not limited to pedestrian crossing buttons, museum interactive display panels, control panels in industrial settings, public phones, internet cafés, keyboards, etc.

Figure 1:
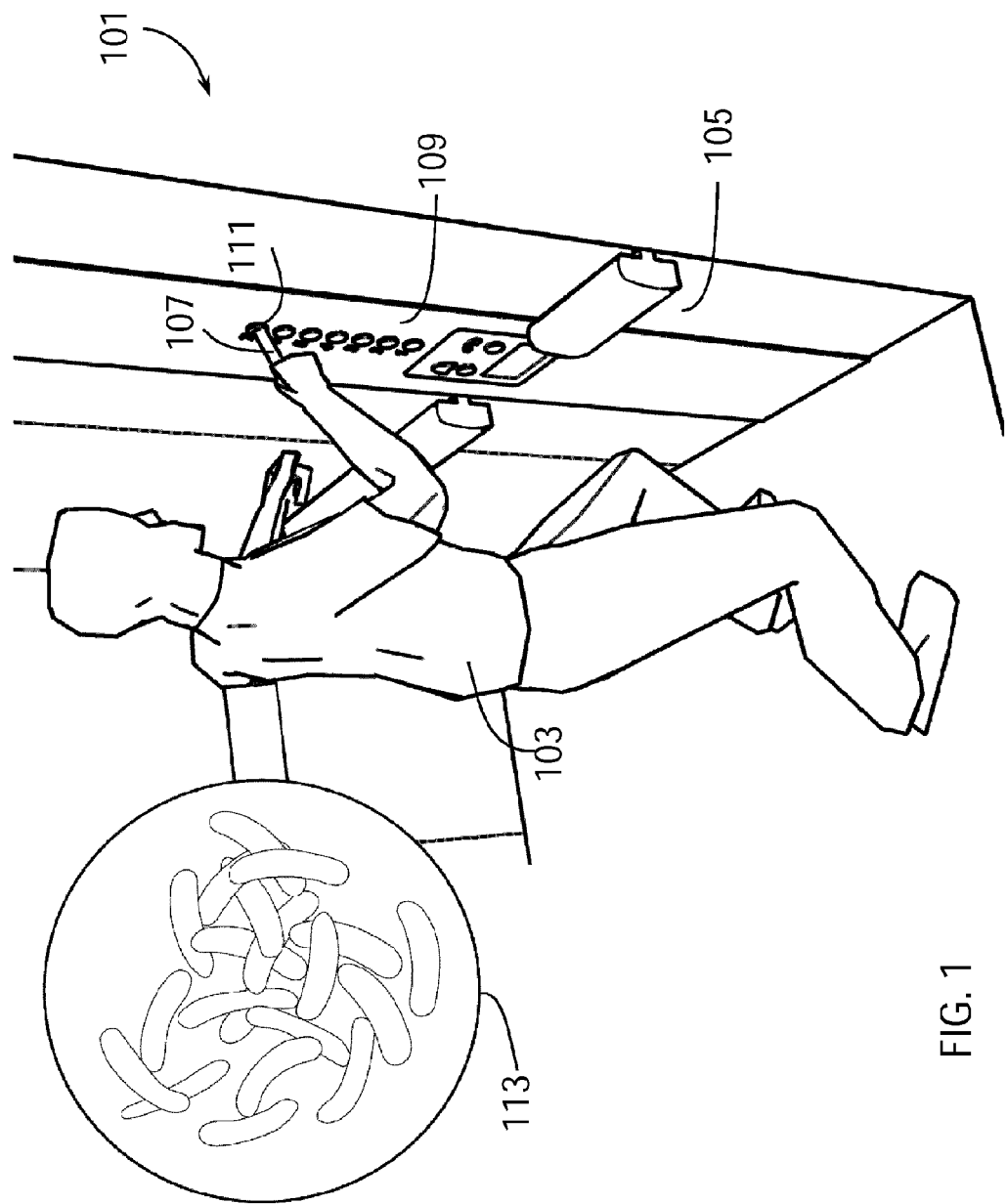
FIG. 1 is a perspective view illustrating a man pressing a button in an elevator.

FIG. 1 shows a man 103 inside in an elevator 105. The man 103 uses his finger 107 to press on a button 111 located on the user panel 109. The physical contact of the finger 107 and the button 111 allows germs and bacteria 113 to be exchanged from the finger 107 to the button 111 and from the button 111 to the finger 107.

The present invention aims at sanitizing the buttons by shining intense shortwave UV light to the exposed button surface. Ultraviolet light kills microorganisms by damaging their DNA. UV photons of wavelength around 250 nm have enough energy to disrupt the chemical bonds that hold the building blocks of DNA together. Specifically this shortwave ultraviolet light disrupts DNA base pairing causing thymine-thymine dimers. If the damage is severe enough, the exposed microorganism cannot repair the damage and rapidly dies. Ultraviolet light affects living organisms but otherwise leaves inorganic material intact. Nothing is emitted except electromagnetic energy. UV radiation is thus preferable over chemical means of sterilization when chemical residues can accumulate and cannot be removed efficiently.

The main challenge in the development of a UV light sanitizer is to prevent exposure to human operators to the UV light. Exposure to UV light can cause eye and skin damage in humans. Thus it is most important to find ways to shield the UV emission using opaque baffles and obstacles. Organizations such as US National Institute for Occupational Safety and Health (NIOSH) recommends that the time of exposure to an intensity of 100 microwatts per square centimeter at wavelength 254 nanometers not exceed 1 minute.

Figure 2:
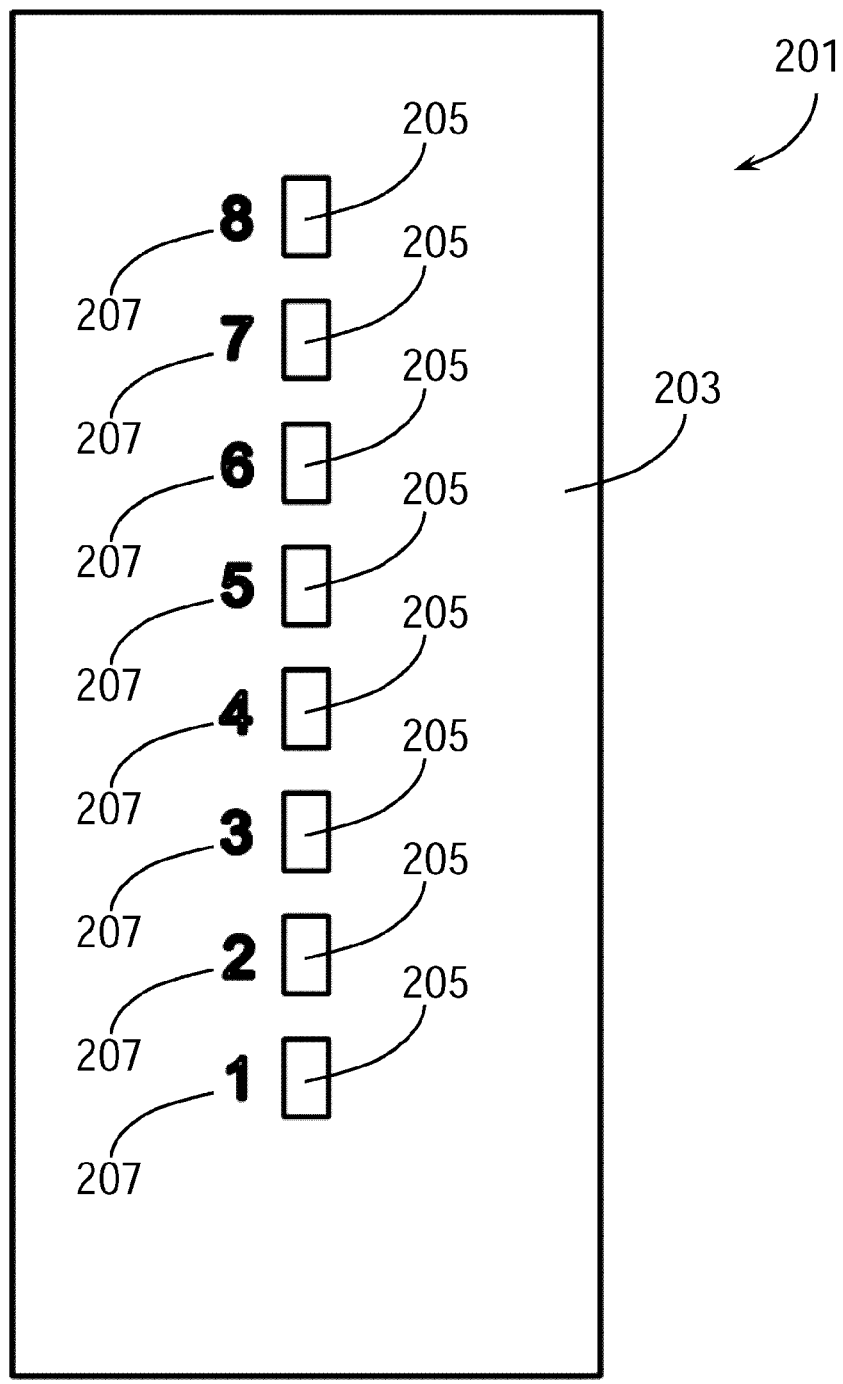
FIG. 2 is a front view of an example user panel with eight buttons.

FIG. 2 to FIG. 8B show one embodiment of the invention. FIG. 2 shows a front view of a housing of the apparatus, for example a user panel 203, featuring eight buttons 205, as seen from the outer side of the panel. These buttons can be assigned to building floors or other elevator functions such as open/close door and alarm call. In the example of FIG. 2, all eight buttons 205 are used to inform the elevator system of a request to go to a particular floor. Eight floor indicators 207 are also shown in FIG. 2. These icons can be made of translucent material and can be illuminated from the rear using low intensity lights 309 such as LED in order to inform the user that the floor call has been registered.

Figure 3:
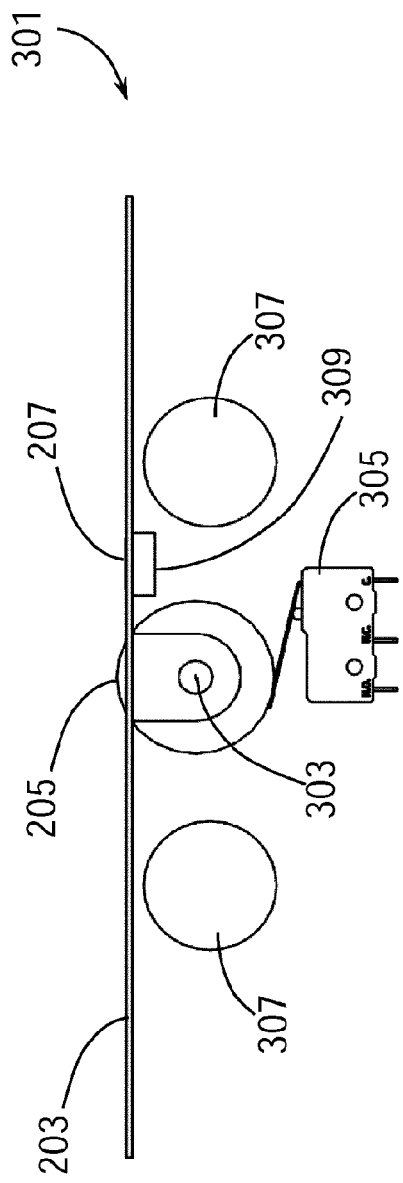
FIG. 3 is a top view of the example user panel shown in FIG. 2 showing cylindrical buttons sanitized using germicidal lamps.

FIG. 3 shows the top view of one possible embodiment of the invention. In this case the buttons 205 are shown to protrude through the user panel 203 towards the user, since they are cylinders mounted on a rod 303, passing through the symmetry axis of the buttons 205. A sensor positioned proximate the buttons for detecting actuation of the buttons, such as an electrical microswitch 305, is mounted behind the button 205. A disinfecting system, such as two germicidal UV lamps 307 located on each side of the button 205, is provided for disinfecting a portion of the buttons 205 that is exposed on the inner side of the panel 203. Although germicidal UV lamps are used in the present example, other disinfecting methods with or without the use of chemical disinfectants can be used. The floor indicators 207 are not visible in FIG. 3, but the rear illumination device 309 is visible.

Figure 4:
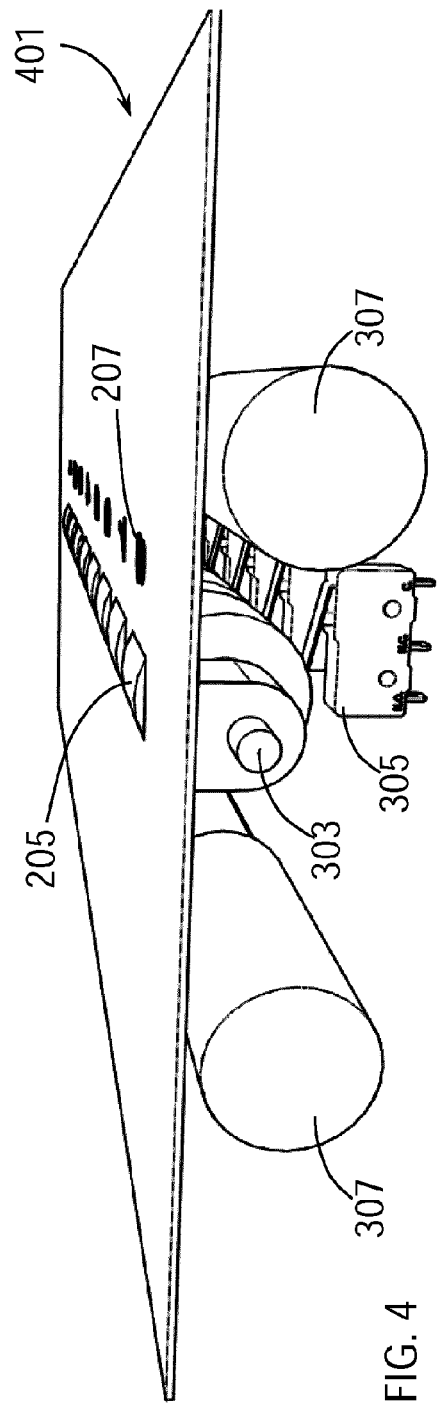
FIG. 4 is a top perspective view of the example user panel shown in FIG. 2 and FIG. 3.

FIG. 4 shows a perspective top view of the example elevator button panel presented in FIG. 3. FIG. 4 illustrates that the buttons 205 are cylindrical.

Figure 5:
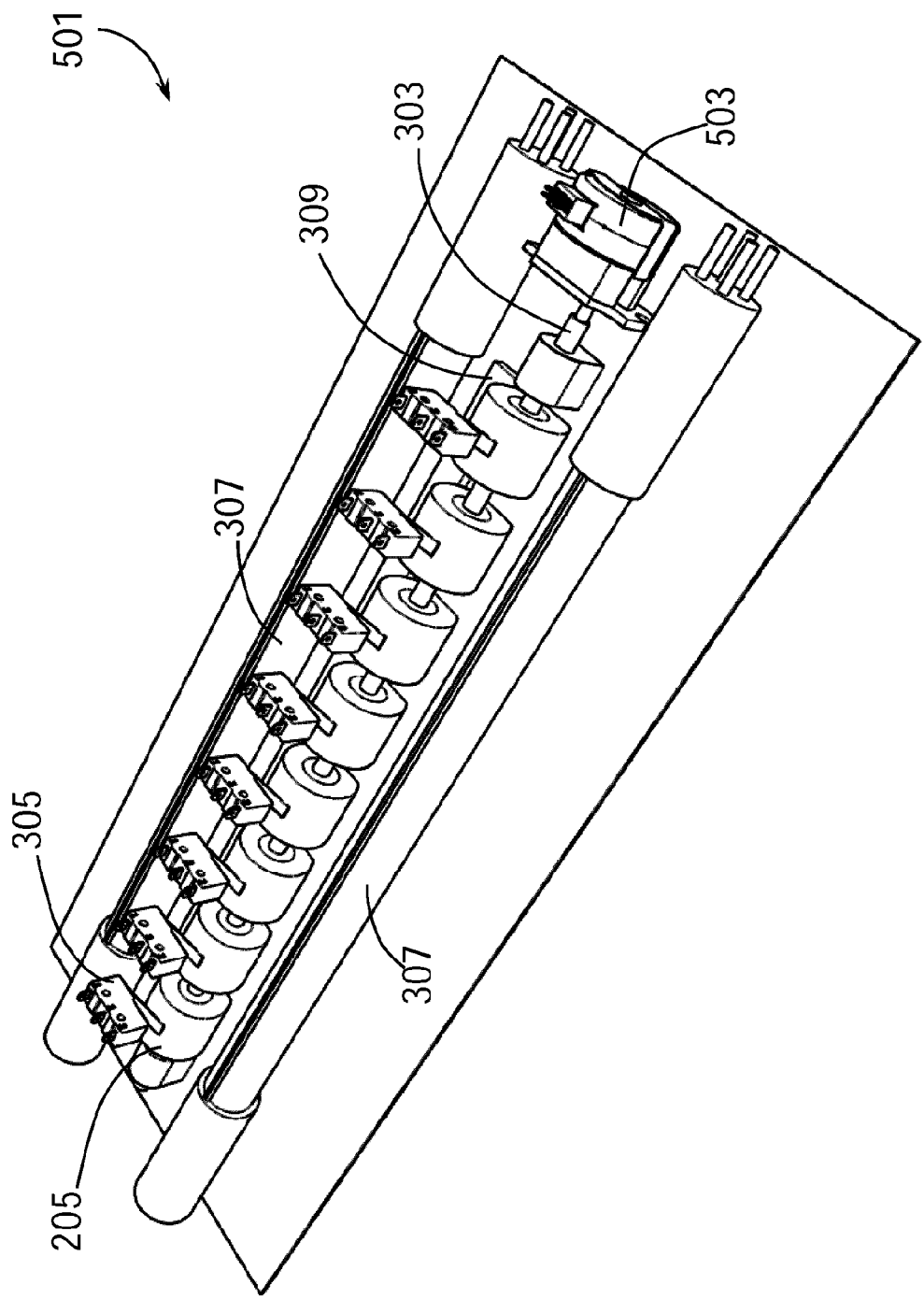
FIG. 5 is a rear perspective view of the example user panel viewed in FIG. 2, FIG. 3 and FIG. 4 showing the motor used to rotate the buttons.

FIG. 5 shows a rear perspective view of the example elevator button panel presented in FIG. 3 and FIG. 4, as seen from the inner side of the panel. In addition to the buttons 205, the electrical microswitches 305, the germicidal UV lamps 307 and the floor indicators illumination device 309, one can see a rotation mechanism, such as a motor 503, whose moving shaft is secured to the mounting rod 303 onto which all buttons 205 are mounted.

The purpose of the rotation mechanism is to slowly rotate the buttons so as to allow surfaces touched by users to be sanitized by the germicidal UV lamps 307. The rotation of the button can be performed in a few different ways. One method consists in imparting a slow, nearly imperceptible, substantially constant rotation so as to make the button appear stationary to the users. This approach has the advantage of avoiding fingers being caught on the entering edge of the button. The rotation speed can be selected in the range between one rotation every 5 minutes to two rotations per minute so as to provide a safe operation and a rapid constant sanitizing of the surface contaminated by the users. Considering that, once pressed, a floor button would normally not be pressed again until the called floor has been reached, the probability of one person touching a surface that was already pressed is low. This is because the floor indicators 207 are lit immediately when someone presses a button, informing others that it is not necessary to press it again.

In the example embodiment of FIG. 5, the ratio of surface exposed to UV light to the surface available to the user on the panel side is large. These large ratios increase the time of exposure to UV light and the effectiveness of the sanitation. It may also allow the use of a lower power germicidal lamp 307.

A variant of this method could use a dual-speed operation for an even lower chance of person-to-person germ transfer. According to this method, the motor can increase the speed of rotation for a fraction of a second immediately after the button is released, fast enough and long enough in order to rotate the soiled surface completely in the sanitizing zone. Thus would ensure that normally behaving users would never touch an unsterilized button surface.

In another embodiment of the invention, the rotation of the button 205 is performed periodically, either after it has been activated (as sensed by the electrical microswitch 305) or periodically based on set time intervals, or when the elevator system detects the absence of a person in the elevator. Other control schemes and combinations are possible as well.

Figure 6:
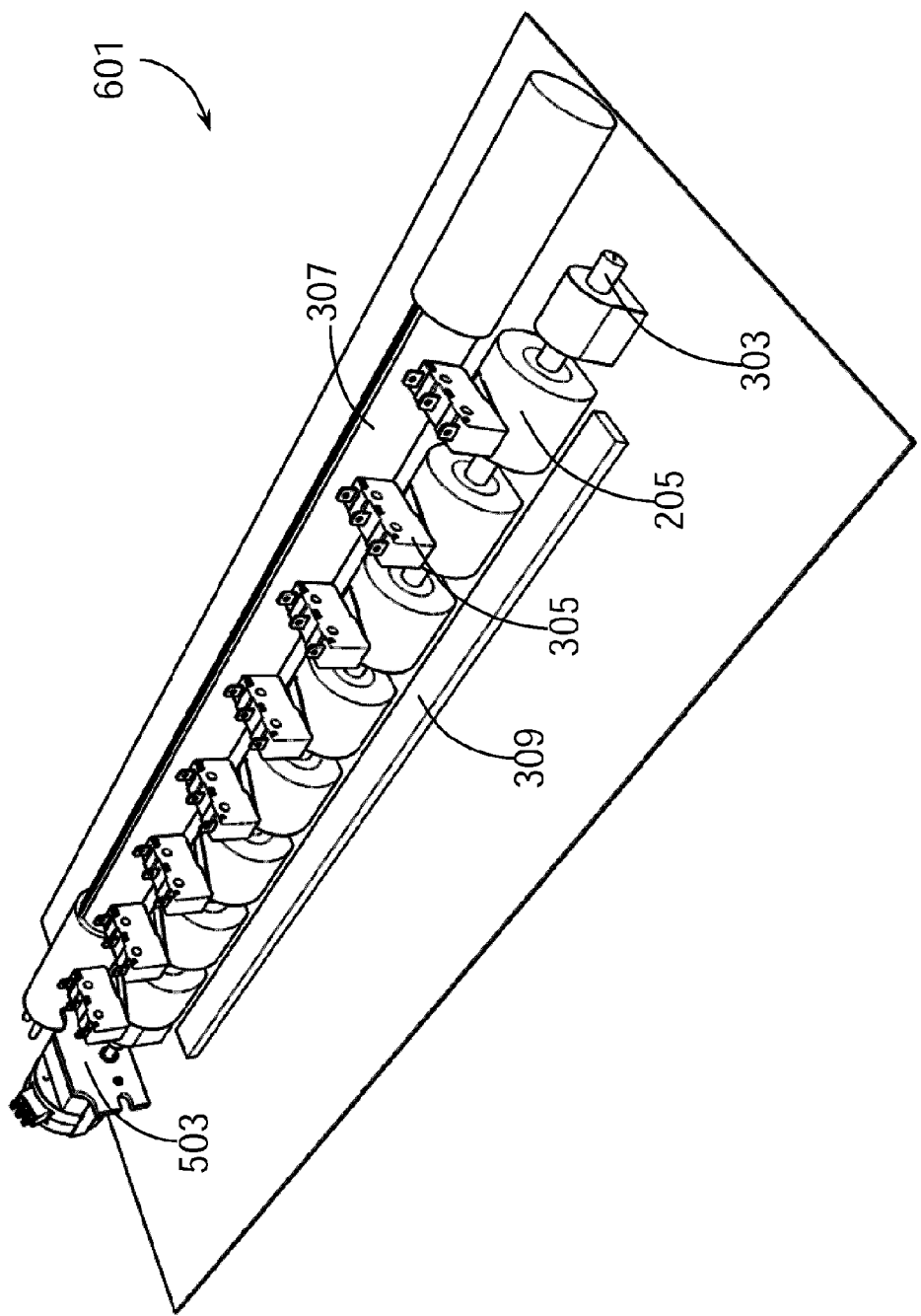
FIG. 6 is another rear perspective view of the example user panel viewed in FIG. 2, FIG. 3, FIG. 4 and FIG. 5 with one of the germicidal lamps removed to better reveal some parts of the assembly.

FIG. 6 shows a different rear perspective view of the example elevator button panel presented in FIG. 3, FIG. 4 and FIG. 5. In this case one of the germicidal UV lamps 307 is removed to offer a better view of the floor indicators illumination device 309. This device is composed of eight individually controllable segments each aligned with one of the floor indicators 207. The elevator controller can turn on and off the appropriate segment based on button calls and the elevator motion sequences.

Figure 7:
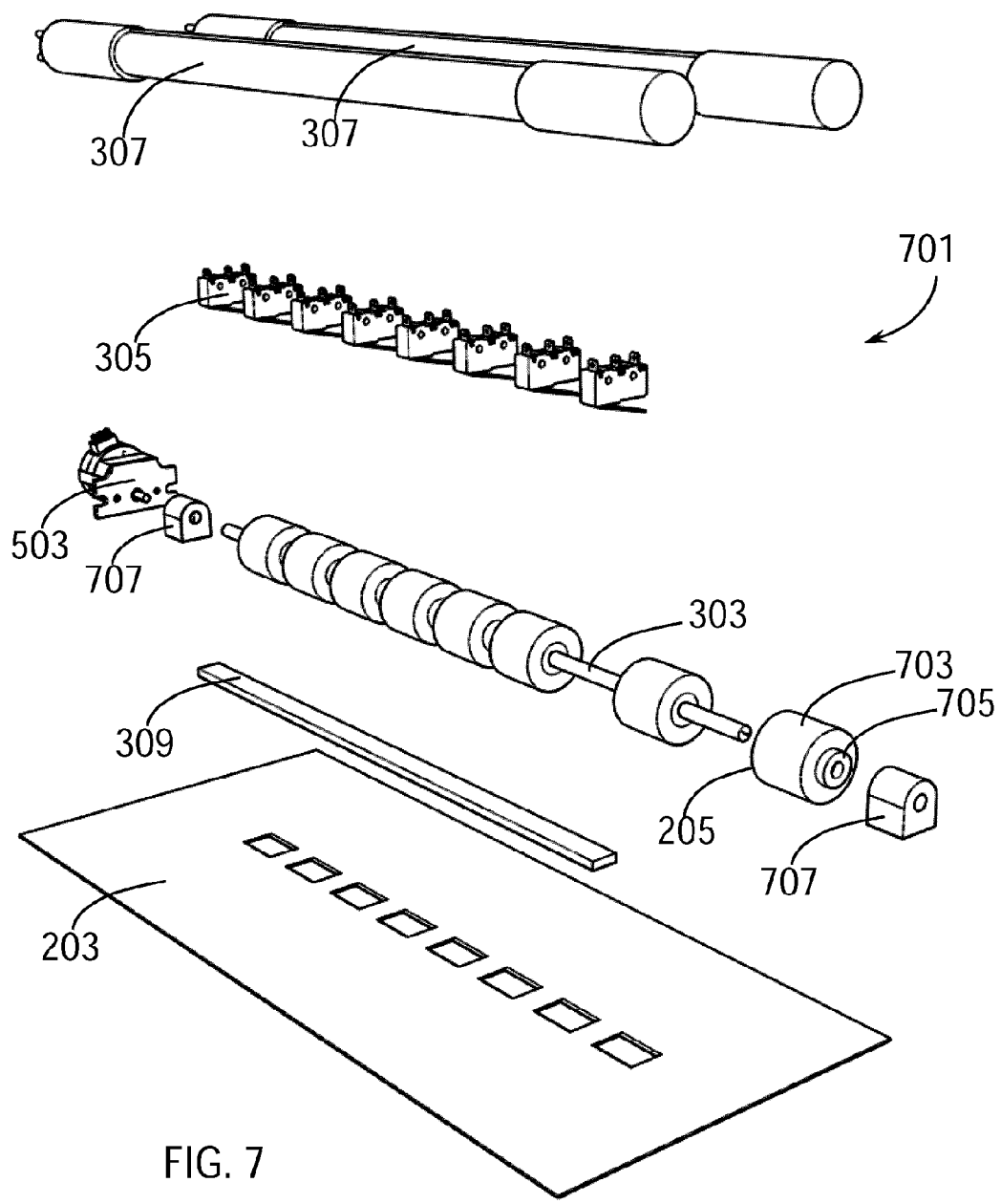
FIG. 7 is an exploded view of the example user panel viewed in FIG. 2, FIG. 3, FIG. 4, FIG. 5 and FIG. 6 showing the parts of the assembly.

FIG. 7 shows an exploded view of the example elevator button panel presented in FIG. 3, FIG. 4, FIG. 5 and FIG. 6. In this image, one button 205 is shown removed from the mounting rod 303 and disassembled in two parts 703 and 705. The outer hollow cylinder 703 can be made of a substantially rigid material such as metal or plastic, while the inner hollow cylinder 705 can be made of an elastic resilient material such as rubber or elastomer. The rod support brackets 707 are mounted on the panel 203 so as to provide support to the mounting rod 303.

FIG. 8A shows a cutout view of one button 205 of the example elevator button panel presented in FIG. 3, FIG. 4, FIG. 5, FIG. 6 and FIG. 7, showing the outer hollow cylinder 703, the inner hollow cylinder 705 mounted on the rod 303. Rotation of the rod about its symmetry axis imparts the rotation motion to the outer hollow cylinder 703 in direction 805 via a mechanical transfer from the inner hollow cylinder 705. Mounting designs that prevent slippage between these three parts can be used.

FIG. 8B shows the same button as FIG. 8A, but being pressed by the finger 807 of a user. The force applied by the finger 807 deforms the non-rigid resilient inner hollow cylinder 705, allowing the outer hollow cylinder 703 to move toward the electrical microswitch 305. The position of the electrical microswitch 305 is adjusted so as to allow triggering by a small motion of the outer hollow cylinder 703.

When the finger 807 is removed from the button 205, the restoring force of the resilient material composing the elastic inner hollow cylinder 705 permits the outer hollow cylinder 703 to return to is resting, symmetrical position as shown in FIG. 8A, thus releasing the electrical microswitch 305. The resilient material composing the inner hollow cylinder 705 is chosen for adequate spring coefficient to provide a pleasant feel during actuation and a low hysteresis to avoid buttons becoming out of alignment and rubbing on the panel 203 during rotation.

Figure 16B:
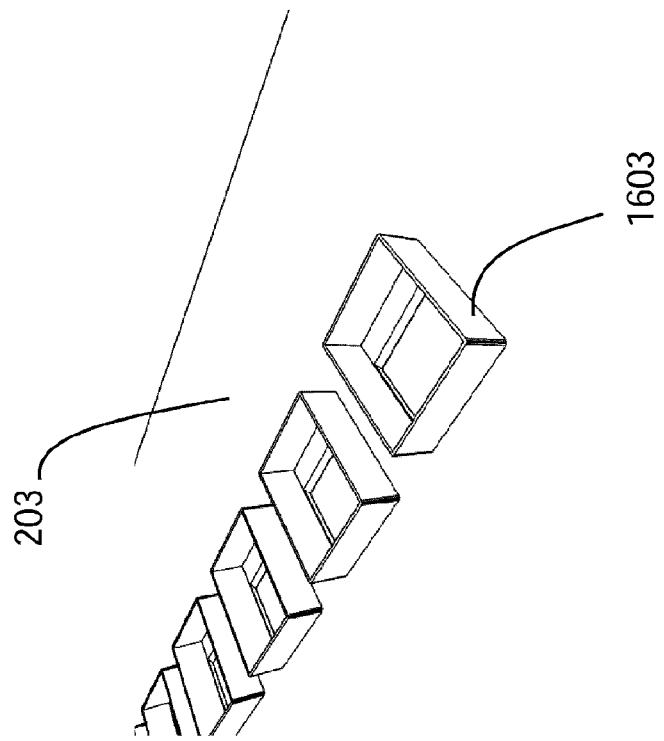
FIG. 16A and FIG. 16B are perspective views of an example skirt assembly to be used between buttons and an elevator panel, with the elevator buttons shown and removed, respectively.
Figure 16A:
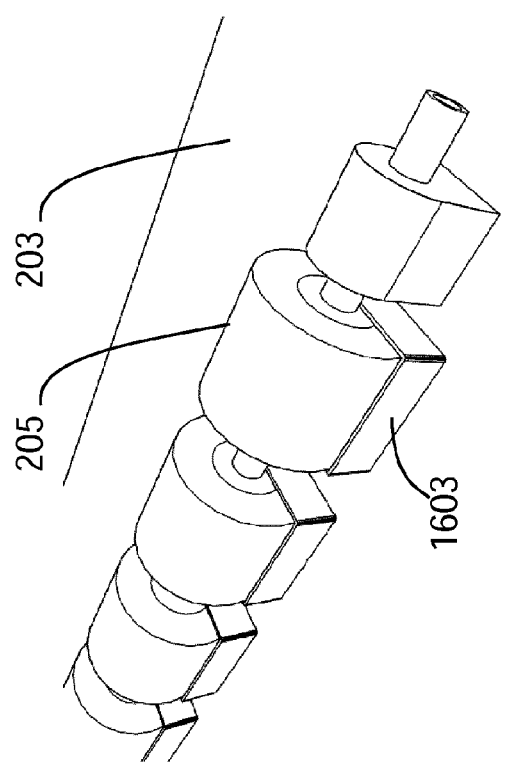

In one embodiment of the invention, as shown in FIGS. 16A and 16B, a skirt assembly 1603 made of metal or UV-proof flexible material can be installed around the hole in the panel 203 to avoid leaks of UV light and allow the use of larger spacing between the button 205 and the panel 203.

Figure 9:
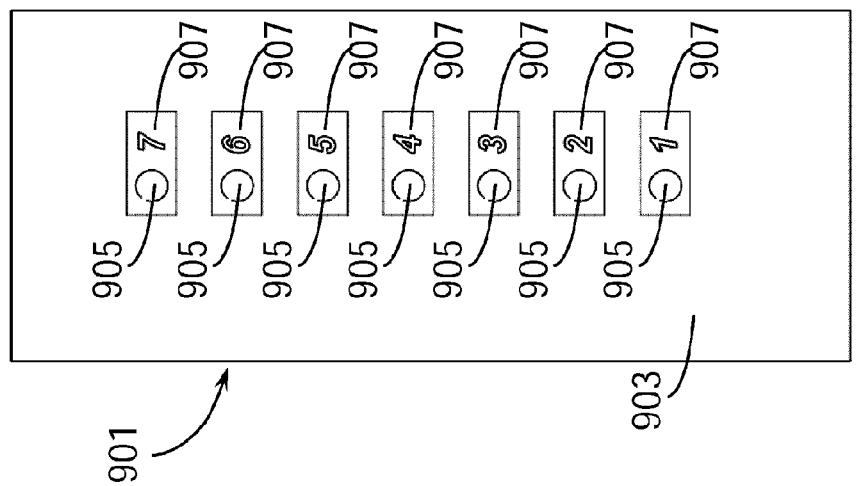
FIG. 9 is a front view of another example user panel with seven buttons.

FIG. 9 to FIG. 12 show another embodiment of the invention. FIG. 9 shows the front view of a user panel 903 featuring seven buttons 905 and accompanying floor indicators 907.

Figure 10:
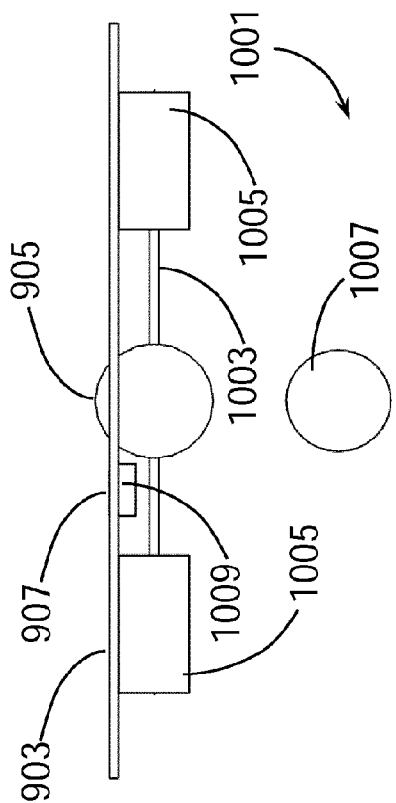
FIG. 10 is a top view of the example user panel viewed in FIG. 9 and showing spherical buttons.

FIG. 10 shows a top view of the user panel presented in FIG. 9. A spherical button 905 is seen mounted on a rod 1003. A UV germicidal lamp 1007 is positioned behind the spherical button 905 allowing sterilization of the rear of the button 905. The floor indicators 907 are not visible in FIG. 10, but the rear illumination device 1009 is visible.

Figure 11:
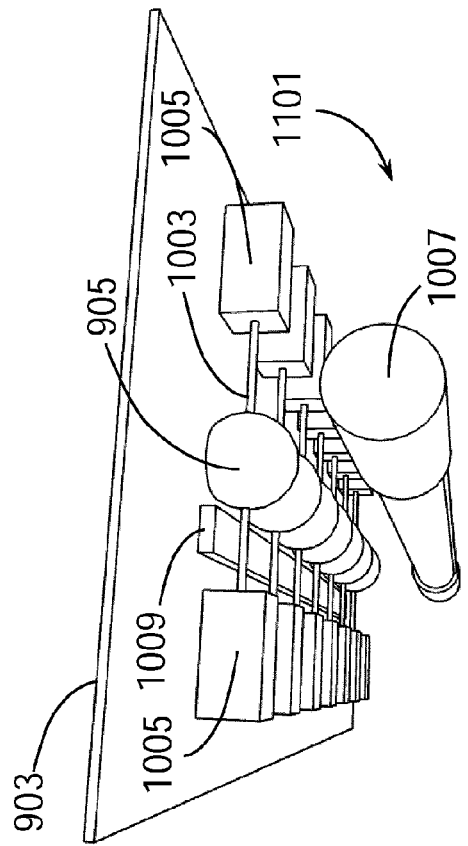
FIG. 11 is a top perspective view of the example user panel viewed in FIG. 9 and FIG. 10, and showing one germicidal lamp.

FIG. 11 shows a perspective top view of the example elevator button panel presented in FIG. 10. FIG. 11 illustrates that the buttons 905 are spherical. Each rod 1003 is mounted on two support assemblies 1005 that provide mechanical support with respect to the panel 903. A motor, which can be installed in one of the two support assemblies 1005, can be used to impart a rotation to each button to allow continuous sterilization. A pivot perpendicular to the rod 1003 but parallel to the plane of the panel 903 can be installed close to the motor allowing the rod to pivot when the user presses the button 905 and allowing to impart a displacement most noticeable at the opposite support assemblies 1005, where an electrical switch can be placed to register the button motion. In another embodiment of the present invention, button non-rotational motion and the use of an external electrical switch can be avoided through the use of a button designed as a pressure-actuated switching device, wherein the button incorporates electrified conductive strips separated by a void space and/or a resilient standoff. Upon application of pressure to the button, the conductive strips are compressed toward each other and make contact, thereby closing an electric circuit, to indicate that the button is actuated. In yet another embodiment of the present invention, the button can be alternatively designed as a capacitive sensor. Capacitive sensors generally operate in two different manners. According to a first approach, a sensor monitors actuation of the button by measuring a change of capacitance of the button through its direct electrical contact with a large capacitive object, usually a person through their finger. According to the second approach, the button includes two conductive planes separated by a compressible, resilient dielectric. The structure of the button thus becomes effectively a capacitor whose capacitance depends in part on the distance between the conductive planes. Actuation of the button results in compression of the dielectric and changes the capacitance between the planes, which can be detected by a sensing system. In both alternate embodiments using the concepts of pressure-actuated switching devices or capacitive sensors, the buttons continue to rotate at a substantially constant speed in order to provide safe operation and a constant sanitizing of the surface of the buttons.

Figure 12:
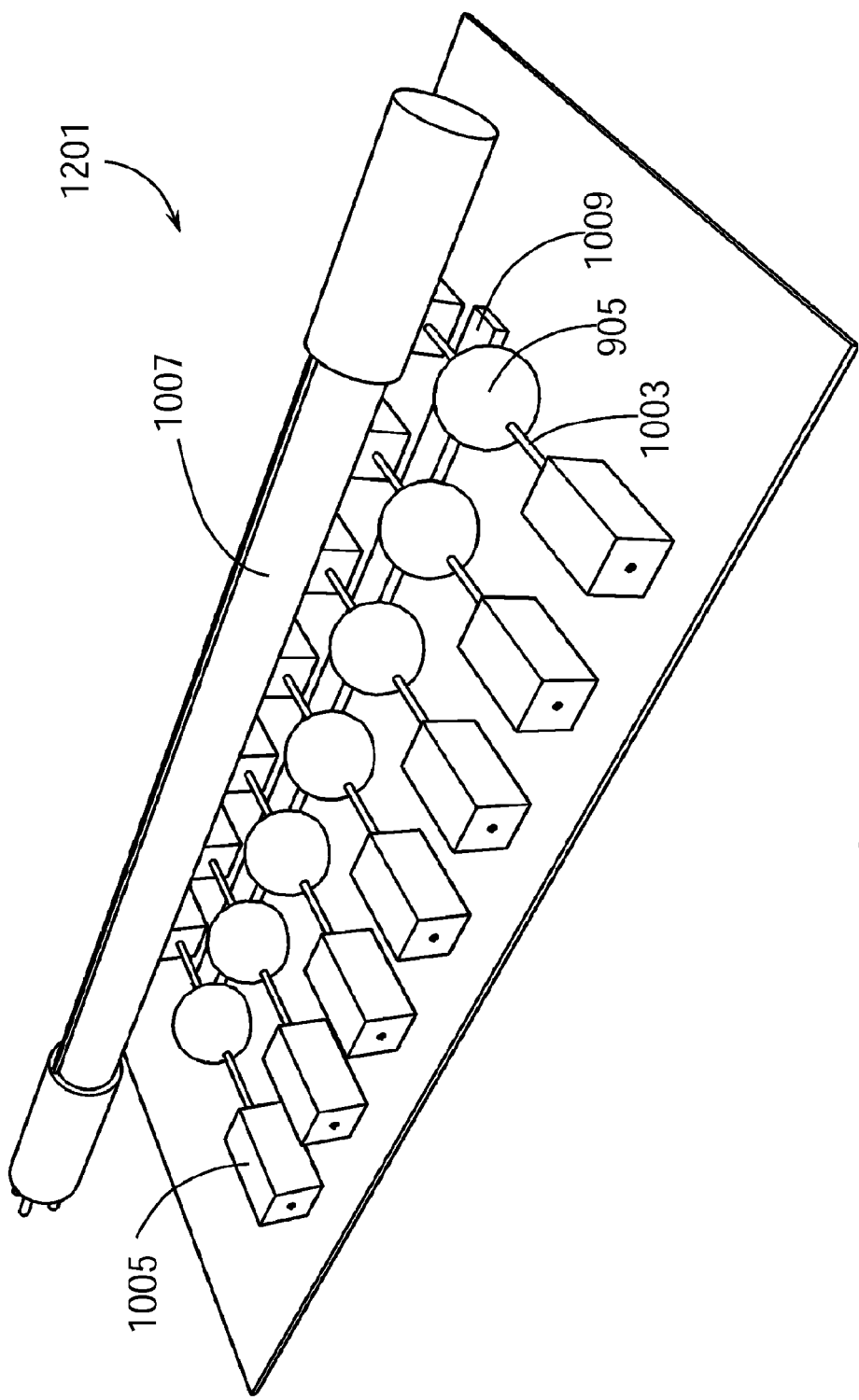
FIG. 12 is a rear perspective view of the example user panel viewed in FIG. 9, FIG. 10 and FIG. 11.

FIG. 12 shows a rear perspective view of the example elevator button panel presented in FIG. 9, FIG. 10 and FIG. 11.

One advantage of the embodiment depicted in FIG. 9 to FIG. 12 is the ability to rotate each button independently. For example this may be beneficial when used with the dual-speed approach described above, to avoid having to rotate all buttons and thus minimize the risk of having a finger pinched if two buttons are pressed almost simultaneously.

Note that the invention can be implemented with shapes of button other than cylinders or spheres as long as they feature a rotational symmetry.

Figure 13B:
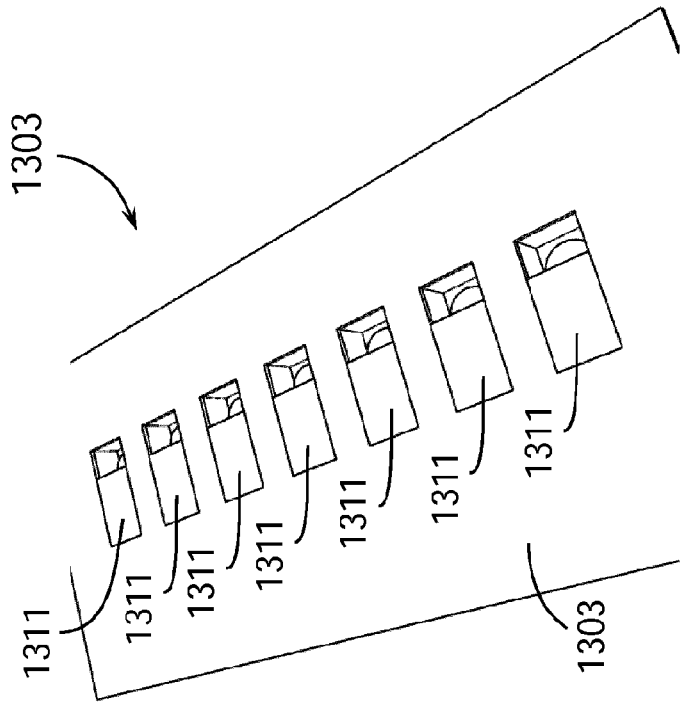
FIG. 13B is a front perspective view of the example user panel viewed in FIG. 13A, with seven doors in the process of enclosing the buttons in their respective recess.
Figure 13A:
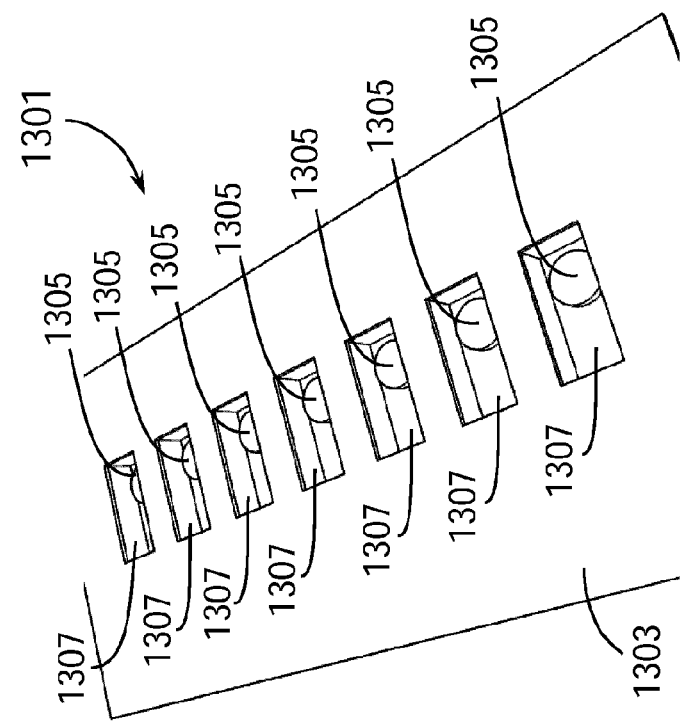
FIG. 13A is a front perspective view of another example user panel with seven buttons each located in a rectangular prism recess.

FIG. 13A to FIG. 15 show yet another embodiment of the invention. FIG. 13A shows the perspective front view of a user panel 1303 featuring seven buttons 1305 each located in an individual recessed rectangular well 1307. Note that the buttons in this case are traditional push buttons and not rotating buttons.

FIG. 13B shows the same front view featured in FIG. 13A, except that each individual recessed rectangular well 1307 is being closed off using individual sliding doors 1311. The purpose of the sliding doors 1311 is to close off the recessed wells 1307 during sterilization to avoid human exposure. The mechanization of the well sliding doors 1311 involves one or several sliding mechanisms and one or several actuators.

FIG. 14 shows a close-up view of one button 1305 located in its recessed well 1307. The short sidewalls 1403 and the long sidewalls 1405 of the button well 1307 can be made of a material transparent to UV light, such as fused silica, to allow sterilization radiation to reach the button 1305 via the short sidewalls 1403 and the long sidewalls 1405.

FIG. 15 shows a rear perspective view of the example user panel presented in FIG. 13A to FIG. 14 and one possible arrangement of UV germicidal lamps 1503 to achieve the sterilization of buttons. Note that the UV germicidal lamps can be positioned close to the panel 1303 in order to maximize the amount of UV light that impinges on the buttons. The internal side of the well covers 1311 can feature a reflective surface, thereby increasing the amount of UV energy impinging on the button surface 1305 thus improving the sterilization process.

Another embodiment of the invention presented in FIG. 13A to FIG. 15 utilizes buttons made of UV transparent material so that the sterilization light can originate from the back of the button and reach its touch surface. In this case, one must also include a cover mechanism or a human exposure avoidance strategy (or both) in order to prevent injury.

The disadvantage of the embodiment presented in FIG. 13A to FIG. 15 is that during the sanitation process, the buttons are not available to the users. This means that the sterilization cannot be performed during usage and thus would offer less protection against germs contagion during heavy use.

The UV lamps in the presented inventions can be traditional mercury-vapor lamps or more recently developed light emitting diodes (LED). The delivery of the UV light can be achieved through free space propagation as illustrated in the figures of this document or can be achieved using light guides or fiber optics.

Note also that depending of the button design, it may be possible to sanitize an individual button after its use, rather than all buttons. This may be useful to conserve energy in systems when individual UV sources are used, notably with LED UV sources.

There exist other exposure avoidance strategies that consist in sensing the presence of humans and shutting off the sanitizing UV lights when such presence is detected. Some modern elevators feature person-sensing technologies such as weight sensors, infrared movement detectors, acoustic sensors, camera-based sensors and proximity sensors, which can be used individually or jointly to ascertain the presence of human beings. However this approach also suffers from intermittent sterilization. Furthermore accidental human exposure to harmful UV rays may be possible because of imperfect human sensing.

The embodiments presented in FIG. 2 to FIG. 8B and FIG. 9 to FIG. 12, are designed to inherently and passively prevent UV light from reaching the users at all times by the elimination of pathways to the user.

In another embodiment of the present invention, the sanitation apparatus may further comprise a UV leak detection system for detecting any possible leaks of UV light emanating from the apparatus housing towards a user. Upon detection of a leak, the UV germicidal lamps would be deactivated as a safety precaution. In one example embodiment, the UV leak detection system could be positioned within the housing, but pointed in the general direction of a user. The UV leak detection system could thus detect any reflection of UV light on a user or any adjacent wall of the elevator, if a leak occurs.

Although the present invention has been explained hereinabove by way of preferred embodiments thereof, it should be pointed out that any modifications to these preferred embodiments within the scope of the appended claims is not deemed to alter or change the nature and scope of the present invention.

The invention claimed is:

1. An apparatus for disinfecting a button comprising:
   a housing having an inner side and an outer side;
   at least one button disposed within the housing, the button having a rotational symmetry allowing rotation of the button with respect to the housing;
   a rotation mechanism for rotating the button with respect to the housing;
   a disinfecting system positioned on the inner side of the housing for disinfecting a portion of the button that is exposed on the inner side of the housing; and
   at least one mounting rod positioned along an axis of rotation of the at least one button, the mounting rod being operatively connected to the rotation mechanism, wherein the rotation mechanism rotates the button at a substantially constant speed and wherein each button comprises a substantially rigid tubular outer portion surrounding a resilient tubular inner portion mounted onto the mounting rod.

2. The apparatus of claim 1, wherein the disinfecting system comprises a ultra-violet germicidal lamp.

3. The apparatus of claim 2, wherein the at least one button is a plurality of elevator buttons and the housing is an elevator button panel.

4. The apparatus of claim 3, wherein the mounting rod connects the plurality of buttons on the inner side of the elevator button panel.

5. The apparatus of claim 1, wherein the at least one button is a plurality of elevator buttons and the housing is an elevator button panel.

6. The apparatus of claim 5 wherein the mounting rod connects the plurality of buttons on the inner side of the elevator button panel.

7. The apparatus of claim 6, wherein the constant speed is between one rotation every five minutes to two rotations per minute.

8. The apparatus of claim 7, further comprising a skirt assembly positioned between the at least one button and the housing for limiting user exposure to the disinfecting system.

9. The apparatus of claim 8, wherein said rotation of the at least one button is momentarily accelerated from said constant speed upon actuation and release of the button by a user and the rotation of the button returns to said constant speed thereafter.

10. The apparatus of claim 1, further comprising a sensor positioned proximate each button for detecting actuation of a corresponding button by a user.

11. The apparatus of claim 10, wherein the sensor is a microswitch.

12. The apparatus of claim 1, wherein the constant speed is between one rotation every five minutes to two rotations per minute.

13. The apparatus of claim 1, further comprising a skirt assembly positioned between the at least one button and the housing for limiting user exposure to the disinfecting system.

14. The apparatus of claim 1, wherein said rotation of the at least one button is momentarily accelerated from said constant speed upon actuation and release of the button by a user and the rotation of the button returns to said constant speed thereafter.

15. The apparatus of claim 1, further comprising a sensor positioned proximate each button for detecting actuation of a corresponding button by a user.

16. The apparatus of claim 15, wherein the constant speed is between one rotation every five minutes to two rotations per minute.

17. The apparatus of claim 16, further comprising a skirt assembly positioned between the at least one button and the housing for limiting user exposure to the disinfecting system.

18. The apparatus of claim 17, wherein said rotation of the at least one button is momentarily accelerated from said constant speed upon actuation and release of the button by a user and the rotation of the button returns to said constant speed thereafter.

* * * * *